(12) United States Patent
Street

(10) Patent No.: US 6,290,707 B1
(45) Date of Patent: Sep. 18, 2001

(54) COSMETIC ABRASIVE PAD AND METHOD FOR SCRUBBING THE EPIDERMIS

(76) Inventor: Vernon D. Street, 5021 Pennington Ave., Baho, MD (US) 21226

(*) Notice: Subject to any disclaimer, the term of this patent is extended or adjusted under 35 U.S.C. 154(b) by 0 days.

(21) Appl. No.: 09/496,976

(22) Filed: Jan. 21, 2000

Related U.S. Application Data

(63) Continuation of application No. 09/192,849, filed on Nov. 17, 1998, now Pat. No. 6,017,351.

(51) Int. Cl.⁷ .................................................. A61B 17/50
(52) U.S. Cl. .............................................................. 606/131
(58) Field of Search ........................ 606/131; 15/104.93, 15/104.94, 227, 229.13, 229.11, 209.1

(56) References Cited

U.S. PATENT DOCUMENTS

| | | | |
|---|---|---|---|
| 2,010,332 | * 8/1935 | Steeg et al. | 132/333 |
| 2,311,060 | * 2/1943 | Lurrain | 606/133 |
| 3,596,661 | * 8/1971 | Motz | 606/131 |
| 3,910,284 | * 10/1975 | Orentreich | 606/131 |
| 4,459,987 | * 7/1984 | Pangburn | 606/131 |
| 5,134,746 | * 8/1992 | William | 15/227 |
| 5,219,340 | * 6/1993 | Seneca | 604/290 |
| 5,346,516 | * 9/1994 | Alkhas et al. | 51/296 |
| 5,609,431 | * 3/1997 | Carroll | 401/201 |

* cited by examiner

Primary Examiner—Gene Mancene
Assistant Examiner—Edvando C. Robert
(74) Attorney, Agent, or Firm—J. Andrew McKinney, Jr.

(57) ABSTRACT

A cosmetic pad for use in removing surface detritus from the skin at pressures a lay person can apply in scrubbing the skin is comprised of a segment of lofty, fibrous, non-woven structure of mixed denier organic (e.g., nylon or polyester) crimped filaments bonded at contacting points with a binder such as thermosetting resin and containing finely divided, biocompatible, soft abrasive particles. The cosmetic abrasive pad of the present invention is advantageously configured for safe, convenient use by a person scrubbing one's self, in the home. In one embodiment of the cosmetic abrasive pad of the present invention, a circular abrasive segment is detachably affixed to a circular handpiece carrying a flexible web bearing hook fasteners on one side and a hand loop or finger loop. The circular handpiece hook fasteners (e.g., Velcro® brand hook fasteners) releasably engage with the fibers of the abrasive segment and permit the user to adjust the position of the abrasive segment on the handpiece. In an alternative embodiment, two substantially rectangular abrasive segments, preferably of differing grades of abrasive aggressiveness, are stitched together on three sides in a laminated structure including two layers of a soft, porous fabric to form a scrubbing mitt having an opening sized to receive a user's hand; the two abrasive segments are positioned on either side and are disposed to present abrasive exterior surfaces having differing grades of abrasive so that a user can use either side by rotating the inserted hand within the mitt to select the appropriate cosmetic abrasive pad surface for scrubbing, to remove detritus or the like from the skin.

9 Claims, 6 Drawing Sheets

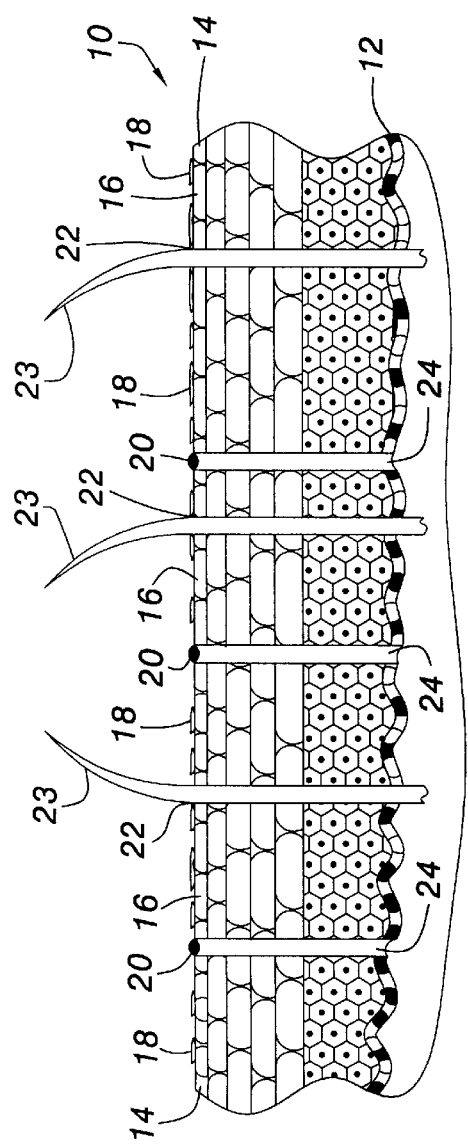
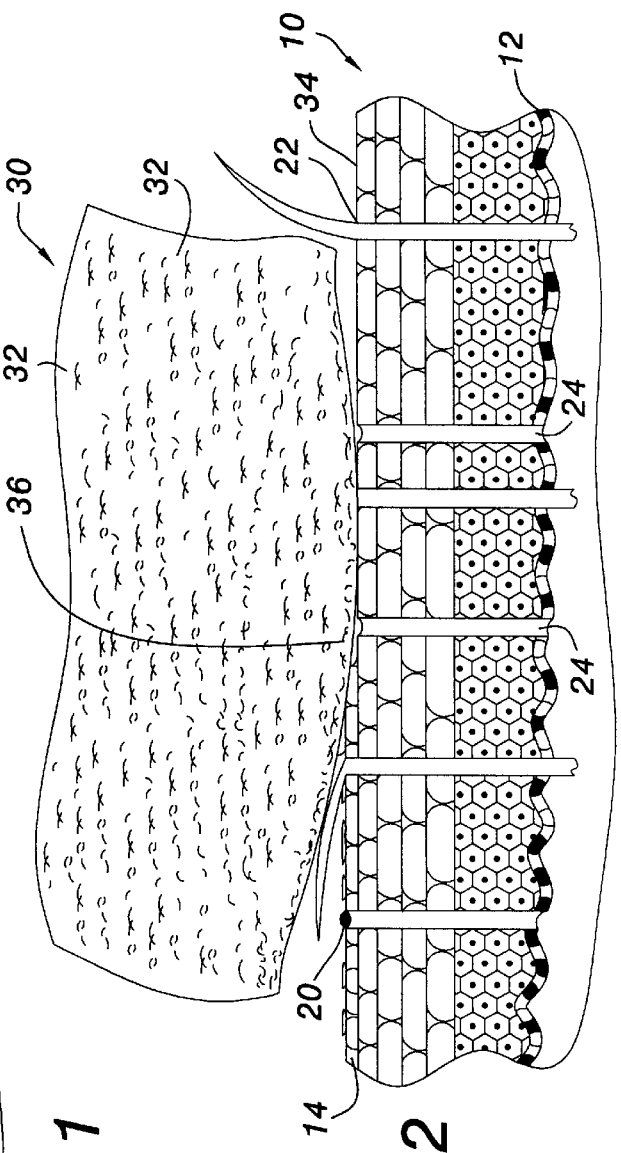

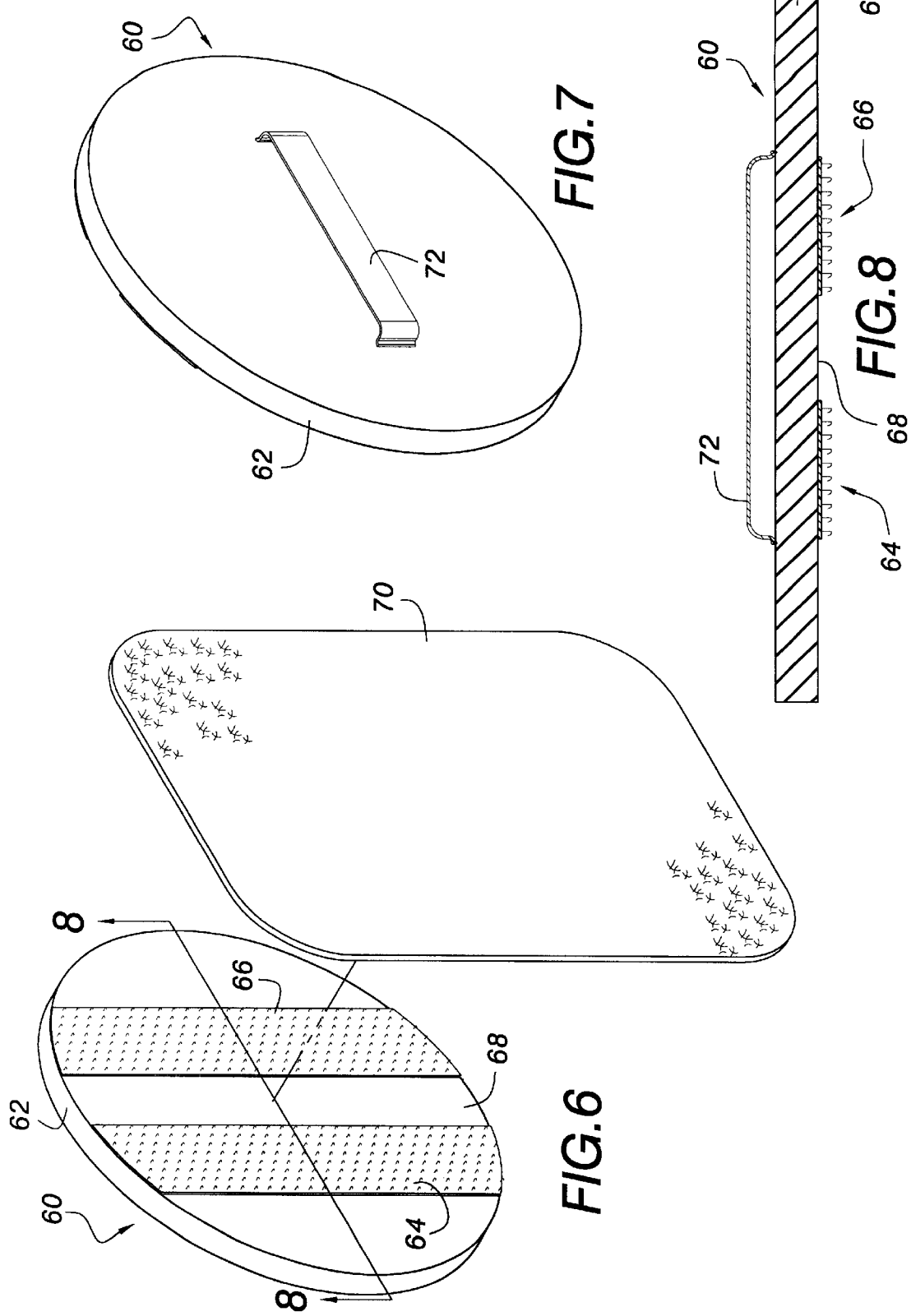

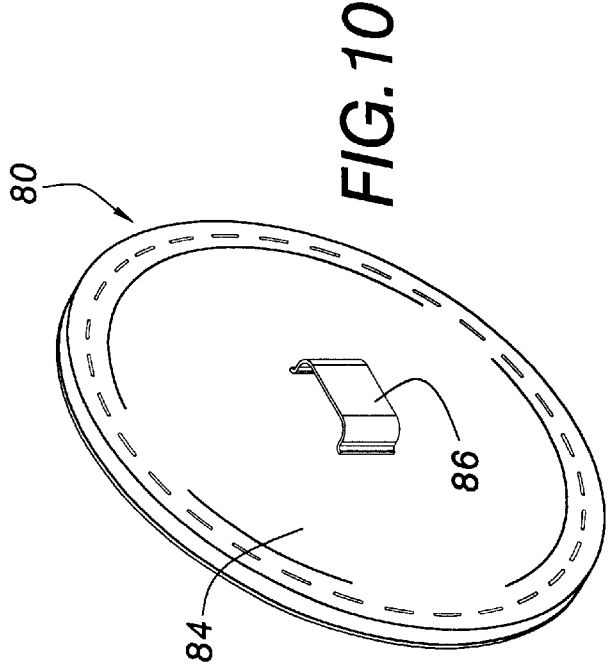
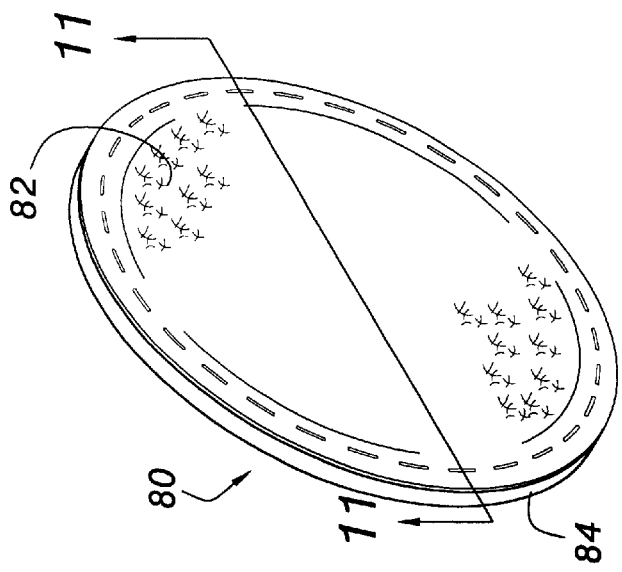
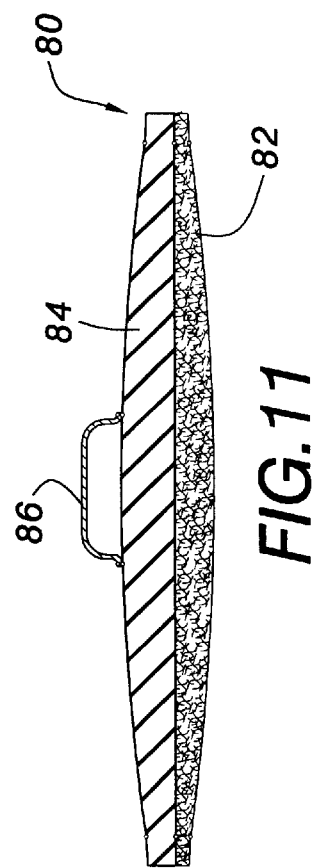

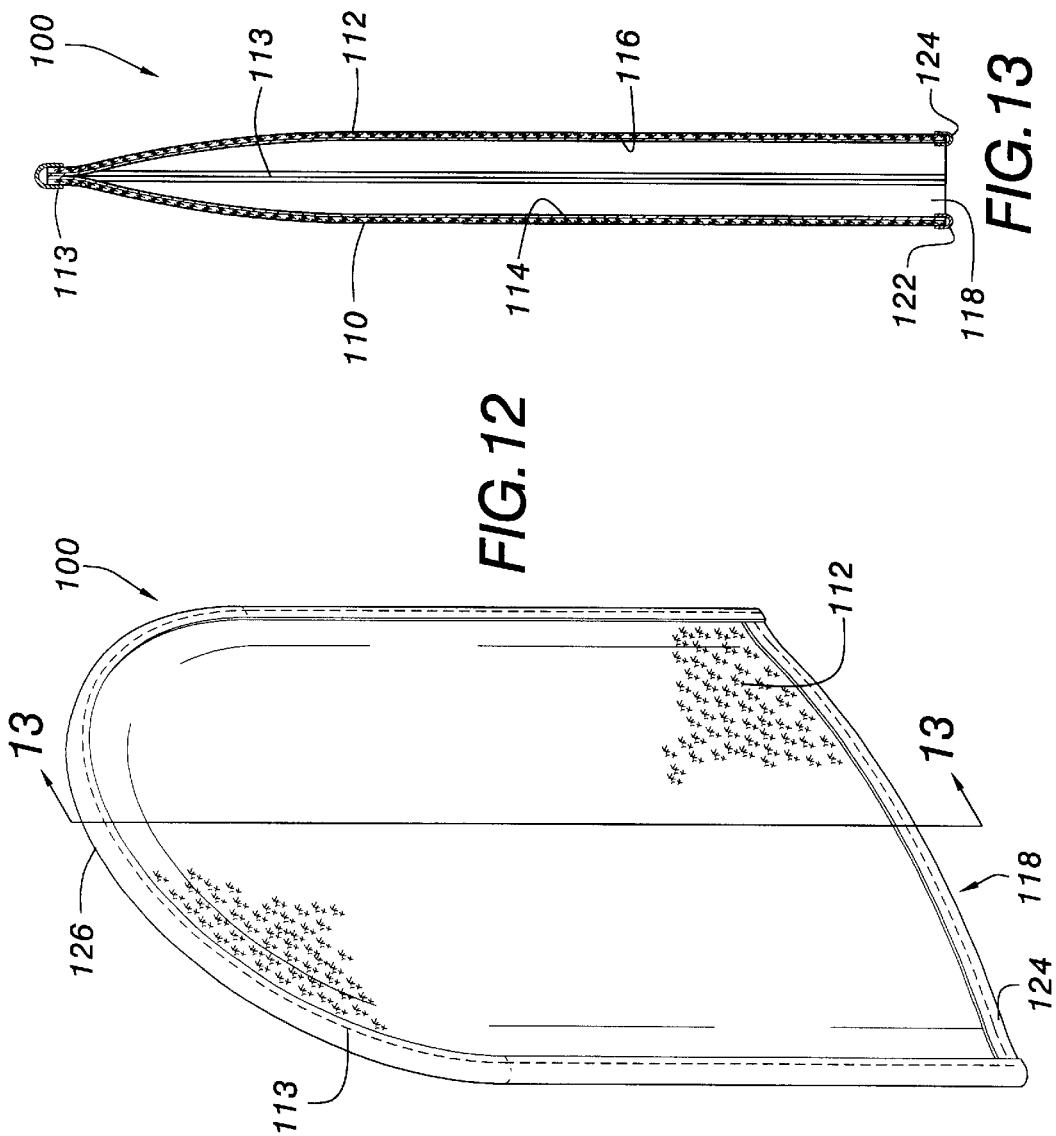

COSMETIC ABRASIVE PAD AND METHOD FOR SCRUBBING THE EPIDERMIS

This application is a continuation application of application Ser. No. 09/192,849, filed Nov. 17, 1998, now U.S. Pat. No. 6,017,351.

BACKGROUND OF THE INVENTION

1. Field of the Invention

The present invention relates to a method and cosmetic abrasive scrubbing pad for scrubbing and removing detritus (such as dead skin or dander), soil and other foreign matter from the epidermis.

2. Discussion of the Prior Art

The skin is an organ separating the inside of the body from the outside world, covers twelve to twenty square feet in area and accounts for 12% of body weight, on average. It is composed of three integrated layers, the epidermis, dermis and subcutis, the layers are referred to as "over skin", "skin" and "under skin". The epidermis is the outermost layer, forming an overall protective covering for the entire body and never more than 0.125 inches thick. At the bottom of the epidermis lies the basal layer in which cell division generates new cells daily. The rate of multiplication for new cells depends on the body's available energy and, in a cycle lasting approximately 27 days, new cells move upwardly through the epidermis, gradually changing from the soft columnar cells of the basal layer from which they are eventually shed. The skin cells are attached to one another by plaques called desmosomes and ascend toward the surface of the over skin in a continuous, impermeable layer. The stratum corneum or horny corneal layer is the outermost part of the epidermis and is comprised of dead epidermal cells averaging 20 cells deep, creating a durable, protective outer barrier for the layers beneath which is resistant to salt and water, further protecting living cells from the damaging effects of excessive dehydration. Excess dead skin cells and sebum accumulate upon the horny corneal layer of the epidermis.

Skin may appear clean and vacant to the naked eye but the number of living organisms on a person's skin is estimated to number in the billions. The flora and fauna of the skin are substantially permanent residents and vary from one region of the body to another, since differing populations of bacteria, mites and yeasts have adapted to specific environments. The dry expanse of the forearm, the dense tangle of the scalp and the oily surface of the nose all harbor particular species. The largest community of the skin's residents are bacteria, usually acquired at birth. Bacteria spreads from person to person both by contact and by constant shedding of dead skin cells. Daily skin loss prevents many would-be colonists from gaining a foothold on the skin. The skin also presents an acidic mantle that deters certain types of bacteria. When the skin's bacteria break down, sebum (fatty acids that increase the skins acidity) are produced. Bacteria thrive in moist areas, so the dryness of the skin may account for part of its resistance to bacterial infections.

The skin plays a prominent role in maintaining the body's temperature. The set point temperature, 98.6° F., is kept in delicate balance; the system is so delicate that if the core temperature varies by 1.5° F. the body's metabolism is altered by about 20%. When the body heat shifts slightly from the set point, the skin's temperature regulation mechanisms quickly restore the proper temperature. The skin achieves this regulation largely by controlling the amount of heat lost. To do so, the skin works in concert with the hypothalamus, a cluster of nerve cells at the center of the brain. Specialized regions of that hypothalamus contain heat sensitive and cold sensitive cells responsive to changes in blood temperature by increasing the number of nerve impulses they transmit. On receiving the hypothalamus commands, the skin hastens to make the appropriate adjustments, restricting blood flow to reduce heat loss or increasing blood flow and activating sweat glands to shed heat. The skin also includes heat receptors and cold receptors which play an important part in detecting temperature changes and permitting precise control of body temperature.

Dirty, unhealthful skin with clogged pores and accumulated detritus such as excess dead skin will not perform the skin's functions as well as healthy, clean skin. Skin care is usually considered to be of paramount importance in maintaining healthy skin and a youthful appearance. The cosmetics industry has devoted considerable resources to the problems of women and men seeking healthy or youthful skin. With age, most people observe that skin becomes increasingly dryer and less elastic and dead skin, dander, flakes and other detritus tend to accumulate on the skin surface (i.e., the over skin or outer epidermis). Accumulated detritus such as dead skin and oxidized sebaceous oil can give rise to a number of skin problems such as formation of comedos or blackheads, resulting in clogged pores. In the prior art, a number of devices have been proposed for scraping, scrubbing or otherwise exfoliating the skin. For example, the exfoliator disc of U. S. Pat. No. 4,438,767, to Nelson, includes a flat circular blade with a circumferential scraping edge for scraping dead skin tissue away. The Nelson scraper is dragged at a selected angle with a selected force to remove dead skin tissue. Being circular, the scraping edge is concave out at a given radius and presents uneven scraping pressure for those parts of the body not having a convex contour with the given radius. Thus, someone using the Nelson scraper cannot apply uniform scraping pressure over even a small area of the body.

Many of the devices of the prior art are intended for use solely by medical professionals such as dermatologists who perform a process known as dermabrasion, wherein rigid abrading stones and other abrading devices are manipulated to remove skin. Rigid abrading devices are not well suited for removing skin from contoured areas such as the elbow or heel and so, even in the hands of a skilled dermatologist, skin "burns" can occur. U.S. Pat. No. 4,459,987, to Pangburn, discloses a flexible abrasive pad intended to permit a dermatologist to remove skin while avoiding creation of skin burns and including a flexible sheet of silicone polymer carrying abrasive particulate and a layer of reticulated, resiliently compressible foam, for light dermabrasion. The Pangburn pad has pumice particulate cured into a silicon sheet and so dead skin or the like will tend to clog and fill the pad as sandpaper clogs when sanding wood. The Pangburn pad must also be used with a selected amount of pressure since the silicon is flexible but transmits the pressure applied directly to the surface being abraded. A dermatologist using the Pangburn pad can rely on his or her professional judgement in deciding how much pressure to apply, when the pad should be cleaned and with what, to avoid problems of skin burn, clogging and filling; lay persons, however, may not be able to use the pad as safely as a dermatologist.

There is a need, therefore, for a method and cosmetic apparatus for safely removing detritus (such as excess dead skin cells or dander), soil or other foreign matter from the epidermis, while overcoming the problems with the prior art as described above.

OBJECTS AND SUMMARY OF THE INVENTION

Accordingly, it is a primary object of the present invention to overcome the above mentioned difficulties by providing a method for removing detritus, soil or other foreign matter from the skin and a specially adapted cosmetic abrasive pad for use in practicing the method.

Another object of the present invention is providing an economical cosmetic method to care for the skin by scrubbing away excess dead epidermal cells.

Yet another object is removing part or all of the dead epidermal cells of the horny corneal layer as part of the cosmetic method for removing surface detritus from the skin.

Another object of the present invention is providing a cosmetic abrasive pad which will be effective for removing surface detritus from the skin at pressures a lay person can readily apply in scrubbing the skin, while avoiding problems of skin burn, filling or clogging.

Yet another object of the present invention is providing a cosmetic abrasive scrubbing pad in a plurality of convenient and effective configurations specially adapted for use on one's self by a lay person, in the home.

The aforesaid objects are achieved individually and in combination, and it is not intended that the present invention be construed as requiring two or more of the objects to be combined unless expressly required by the claims attached hereto.

In accordance with the method of the present invention, the outer layer of the epidermis and any detritus or foreign matter on the skin is removed by a scrubbing motion tending to abrade away part or all of the dead epidermal cells of the horny corneal layer of the epidermis and any comedos or blackheads embedded therein. A cosmetic abrasive pad for scrubbing the epidermis in accordance with the present invention includes a lofty non-woven, open abrasive pad being light in weight, extremely open throughout, providing a non-clogging and non-filling nature and permitting the pad to be used in the bath with or without lotions or soaps, where detritus, soap scum and other residues clog prior art abrasive devices. The cosmetic abrasive pad of the present invention is substantially rectangular or circular in shape and is sized conveniently to be held in the user's hand or formed as a mitt or pad having a finger retaining band. The cosmetic pad is comprised of a segment of lofty, fibrous, non-woven structure of mixed denier nylon or polyester crimped or bent filaments bonded at contacting points with a binder such as thermosetting resin or the like and containing finely divided, biocompatible, soft abrasive particles.

In an alternative embodiment, the cosmetic abrasive pad includes a first surface having a mildly abrasive nature and a second surface having a more aggressively abrasive nature; the abrasive particles on both sides are biocompatible, however, and so are not intrisically toxic, injurious or likely to cause an adverse immunological reaction. Soft abrasive particles are incorporated into the mildly abrasive surface and are capable of cleaning the softest skin as is found on the face and around the eyes. The second surface provides an aggressive, abrasive surface capable of softening and scouring away tougher, thickened dead calloused skin as is found on the heels, palms and the like. The cosmetic pad of the present invention is readily cleaned by rinsing with warm water or the like to remove accumulated dead skin and other detritus. After use, the pads may be conveniently dried and left for substantial periods of time and then reused.

The cosmetic abrasive pad of the present invention is more specifically described as a uniform, lofty, open, non-woven, three-dimensional, lightweight web formed of many interlaced randomly disposed, flexible, durable, tough organic fibers exhibiting substantial resiliency and strength upon prolonged subjection to water, oils, soaps or cosmetic lotions. Fibers of the web are preferably bent or crimped nylon or polyester and are firmly bonded together at points where they intersect and contact one another by globules of an organic (e.g., resin) binder, thereby forming a three-dimensionally integrated structure. Distributed within the web and firmly adhered by binder globules at variously spaced points along the fibers are biocompatible abrasive particles. The many interstices between adjacent fibers remain substantially unfilled by the binder and abrasive particles, thereby providing a composite structure of extremely low density having a network of many relatively large intercommunicated interstitial voids. The voids preferably make up approximately three-fourths or more of the total volume occupied by the composite structure. The resulting abrasive cosmetic pad structure is flexible and readily compressible and, upon subsequent release of pressure, essentially completely recovers to the initial uncompressed form. The resulting lightweight, lofty, extremely open, fibrous, abrasive construction exhibits a remarkably effective and unique abrasive action and, in use, acculates detritus; the padis essentially non-clogging and non-filling in nature, particularly when used in conjunction with liquids such as water or cosmetic lotions or oils. Since the fibers are resilient and yieldable, the biocompatible abrasive particles are extremely effective at removing dead skin or other detritus from the epidermis at pressures a lay person would use when scrubbing one's self.

Commercially available uniform, lofty, open, non-woven, three-dimensional, lightweight abrasive web material is available from Minnesota Mining and Manufacturing Company and is sold for commercial and industrial applications under the tradename SCOTCH-BRITE™, as described in U.S. Pat. No. 2,958,593 to Hoover et al, U.S. Pat. No. 4,078,340 to Klecker et al and U.S. Pat. No. 5,363,604 to Heyer, the entire disclosures of which are incorporated herein by reference. Others have produced non-woven, lofty open three dimensional webs, such as disclosed in U.S. Pat. No. 5,346,516 to Alkhas et al, the entire disclosure of which is incorporated herein by reference; the Alkhas patent also discloses an abrasive suitable for industrial applications. In the prior art, such pads have costomarily been used for abrading away hardened putty in autobody work, stripping wax with commercial floor cleaners and several other commercial and industrial applications.

By using relatively non-aggressive and biocompatible abrasive particles, such as pumice, a cosmetic abrasive pad including a uniform, lofty, open, non-woven, three-dimensional, lightweight web formed of many interlaced randomly disposed, flexible, durable, tough organic fibers exhibiting substantial resiliency and strength upon prolonged subjection to water, oils, soaps or cosmetic lotions is produced and is usable in the method of the present invention.

The cosmetic abrasive pad of the present invention is advantageously configured for safe, convenient use by a person scrubbing one's self, in the home. In one embodiment of the cosmetic abrasive pad of the present invention, a circular segment of lofty, fibrous, non-woven structure of preferably mixed denier organic (e.g., nylon or polyester) crimped filaments bonded at contacting points with a binder such as thermosetting resin or the like and containing finely divided, biocompatible, soft abrasive is detachably affixed to a substantially planar, flexible, circular handpiece carrying a flexible web bearing hook fasteners on one side and a hand loop of finger loop. For purposes of less cumbersome exposition, the "segment of lofty, fibrous, non-woven structure of mixed denier organic (e.g., nylon or polyester) crimped filaments bonded at contacting points with a binder such as thermosetting resin or the like and containing finely divided, biocompatible, soft abrasive" will be referred to simply as "abrasive segment".

The circular handpiece hook fasteners (e.g., VELCRO® brand hook fasteners) releasably engage with the fibers of the abrasive segment and permit the user to adjust the position of the abrasive segment on the handpiece. In a preferred embodiment, the hook fasteners are carried on two nearly semicircular segments stitched on the handpiece with an elongate gap therebetween, thus permitting the user to manipulate and bend the handpiece readily along the elongate gap, so that the cosmetic abrasive pad of the present invention can be readily folded or bend around contours of the body while scrubbing. The user can reverse the abrasive segment by switching the side engaged with the hook fasteners, thereby permitting the use of both sides of the abrasive segment. When one side of the abrasive segment begins to shown signs of wear, the user can easily reverse the abrasive segment to expose the fresh, unused side.

In an alternative embodiment, two substantially rectangular abrasive segments, preferably of differing grades of coarseness or abrasive aggressiveness, are stitched together on three sides in a laminated structure including two layers of a soft, porous fabric to form a scrubbing mitt having an opening sized to receive a user's hand. The two layers of soft fabric are layered together and form an interior lining. The two abrasive segments are positioned on either side and are disposed to present abrasive exterior surfaces, preferably having differing grades of abrasive so that a user can use either side by rotating the inserted hand within the mitt to select the appropriate cosmetic abrasive pad surface for scrubbing, to remove detritus or the like from the skin.

In a third embodiment, a substantially rigid, elongate member is wrapped on one end with an abrasive segment. The unwrapped end serves as a handle, thus permitting the user to insert the abrasive-wrapped elongate member into body crevices and between toes, or the like, to remove detritus in what were hitherto unreachable locations.

In the cosmetic method of the present invention, a user removes detritus including dead skin cells, oxidized sebum, soil, and other foreign matter from the horny corneal layer of the epidermis by grasping the cosmetic abrasive pad of the present invention including the abrasive segment, and wiping the surface of the epidermis with the cosmetic abrasive pad to remove at least part of the dead skin cells of the horny corneal layer of the epidermis and accumulating the removed dead skin cells in the lofty, fibrous, non-woven structure of the abrasive segment.

The above and still further objects, features and advantages of the present invention will become apparent upon consideration of the following detailed description of a specific embodiment thereof, particularly when taken in conjunction with the accompanying drawings, wherein like reference numerals in the various figures are utilized to designate like components.

BRIEF DESCRIPTION OF THE DRAWINGS

FIG. 1 is a cross sectional illustration of the epidermal layer including the over skin or horny corneal layer and shows an accumulation of detritus including a number of pore blockages or blackheads formed from oxidized sebum.

FIG. 2 is a cross sectional illustration of the epidermal layer of FIG. 1 partially scrubbed to remove a portion of the horny corneal layer along with the detritus and pore blockages and showing that the accumulated detritus is accumulated within the lofty fibrous non-woven structure of the cosmetic abrasive pad of the present invention.

FIG. 6 illustrates an alternative embodiment of the cosmetic abrasive pad of the present invention having a larger circular hand piece bearing two strips of hook fasteners for attachment to a substantially rectangular abrasive pad segment.

FIG. 7 shows the reverse or hand-loop side of the cosmetic abrasive pad of FIG. 6.

FIG. 8 is a cross sectional illustration of the cosmetic abrasive pad of FIG. 6, taken along line 8—8 as shown in FIG. 6.

FIG. 9 illustrates a small, substantially circular cosmetic abrasive pad of the present invention with a permanently stitched or attached circular abrasive segment.

FIG. 10 shows the reverse or finger-loop side of the cosmetic abrasive pad of FIG. 9.

FIG. 11 is a cross sectional illustration of the cosmetic abrasive pad of FIG. 9, taken along line 11—11 as shown in FIG. 9.

FIG. 12 illustrates a cosmetic abrasive pad mitt of the present invention with first and second permanently stitched or attached abrasive segments.

FIG. 13 is a cross sectional illustration of the cosmetic abrasive pad mitt of FIG. 12, taken along line 13—13 as shown in FIG. 12.

DESCRIPTION OF THE PREFERRED EMBODIMENT

Figure 3:
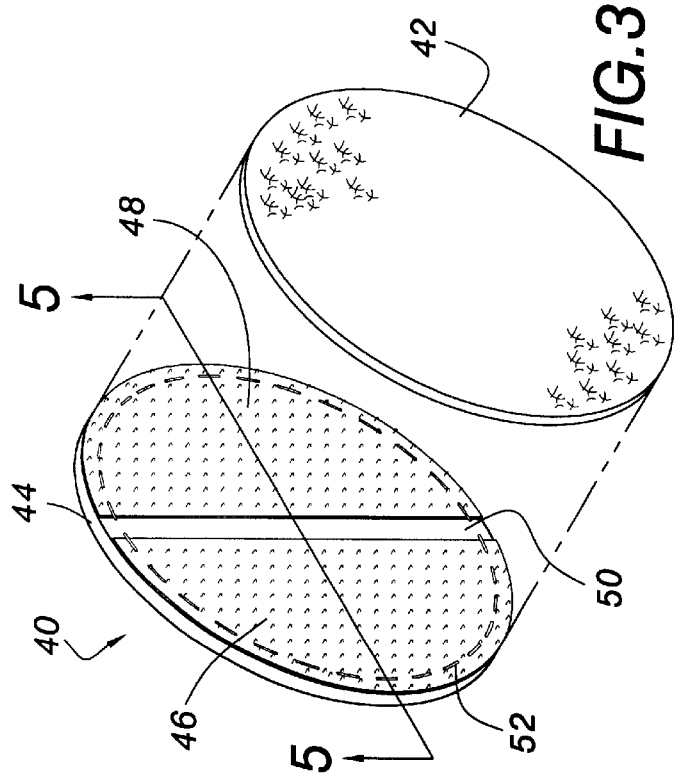
FIG. 3 illustrates a small, substantially circular cosmetic abrasive pad of the present invention with a circular abrasive segment releasably attachable on hook fasteners.

FIG. 1 illustrates a cross section of the skin's epidermal layer 10 and shows the basal layer 12 disposed beneath the many layers covered by the outer stratum cornium or horny corneal layer 14 consisting of dead epidermal cells 16 in the layered or laminated structure described above. Excess dead skin cells 18 and solid plugs of oxidized sebum (otherwise known as comedos or blackheads) 20 are included in the detritus on the outer skin surface. The epidermal layer of the skin 10 has a plurality of hair follicles 22 from which individual hairs 23 grow and pores 24 in fluid communication with the sweat glands (not shown) disposed beneath the basal layer 12. The blackheads or plugs 20 tend to clog or block the pores 24 or follicles 22, often leading to unhealthful complications. As shown in FIG. 2, according to the method of the present invention, the detritus including dead skin cells 18 and plugs of oxidized sebum 20 are removed as by exfoliation along with, optionally, some or all of the dead skin cells of the horny corneal layer 14, by a wiping or scrubbing application of the cosmetic abrasive pad 30 of the present invention. Pad 30, shown in cross section in FIG. 2, is comprised of a segment of lofty, fibrous, non-woven structure of mixed denier organic (e.g., nylon or polyester) crimped or bent filaments bonded at contacting points with a binder such as thermosetting resin or the like and containing uniformly distributed finely divided biocompatible soft abrasive particles. The biocompatible abrasive particles are preferably pumice or the like. Cosmetic abrasive pad 30 has a lofty open structure having extremely low density and a network of many relatively large and intercommunicated interstitial voids 32. The voids 32 preferably make up approximately three-quarters or more of the total volume occupied by the composite structure of the abrasive segment of cosmetic abrasive pad 30 and the scrubbed off dead skin cells 16, detritus 18 and plugs 20 are readily removed and accumulated within the voids 32 as cosmetic abrasive pad 30 is wiped or scrubbed across the outer surface of the epidermis 10. As best seen on the right side of FIG. 2, the pad, wiping from right to left, has removed all detritus 18 and dead skin cells 16 of the horny corneal layer 14 from the scrubbed or exfoliated surface 34 of the epidermis 10 and accumulated the detritus 36 within the voids 32 of the lofty open structure of cosmetic abrasive pad 30. As cosmetic abrasive pad 30 wipes right to left along the surface of the epidermal layer 10, the voids 32 will progressively continue to fill with detritus 36 including dead skin cells. Once the user has completed wiping or scrubbing the skin, the accumulated detritus 36 is readily rinsed or washed from the cosmetic abrasive pad of the present invention.

Figure 4:
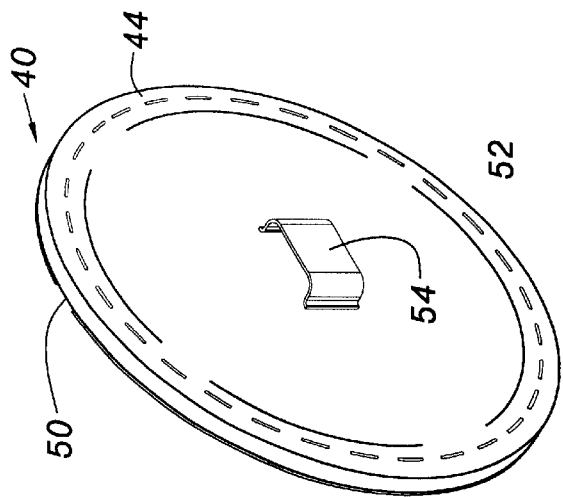
FIG. 4 shows the reverse or finger-loop side of the cosmetic abrasive pad of FIG. 3.
Figure 5:
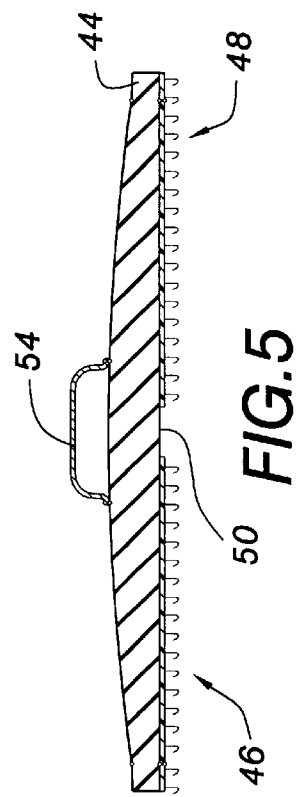
FIG. 5 is a cross sectional illustration of the cosmetic abrasive pad of FIG. 3, taken along line 5—5 as shown in FIG. 3.

Turning now to FIGS. 3, 4 and 5, there is illustrated an embodiment of the cosmetic abrasive pad 40 in accordance with the present invention. Cosmetic abrasive pad 40 is advantageously configured for safe, convenient use by a person scrubbing oneself in the home and includes an abrasive segment 42 comprising a substantially circular segment of lofty, fibrous, non-woven structure of preferably mixed denier organic (e.g., nylon or polyester) preferably crimped or bent filaments bonded at contacting points with a binder such as a thermosetting resin or the like and containing finely divided, biocompatible, soft abrasive. Abrasive segment 42 is detachably attached to a substantially circular and planar flexible hand piece 44 having a finger loop side opposing an abrasive retaining side and carrying a first substantially semicircular array of hooks 46 and a second substantially semicircular array of hooks 48 on the abrasive retaining side and separated by an elongate gap 50, as best seen in FIGS. 3 and 5. The two nearly semicircular hook fasteners arrays 46, 48 include a plurality of hook fasteners (e.g., VELCOR® brand hook fasteners) and releasably engage the fibers of abrasive segment 42 permitting the user to adjust the position of abrasive segment 42 on hand piece 44. The user can manipulate and bend or flex hand piece 44 along the elongate gap 50 so that cosmetic abrasive pad 40 can be readily folded or bent around contours of the body while scrubbing in accordance with the method of the present invention. The user can reverse abrasive segment 42 by switching the side engaged with the hook fastener arrays 46, 48 thereby permitting the use of both sides of abrasive segment 42 before cleaning accumulated detritus out of the abrasive segment. When one side of abrasive segment 42 begins to show signs of wear, the user can also easily reverse the abrasive segment to expose the fresh, less worn side.

The abrasive segment 42 can be any of a number of attractive colors, including green, burgundy, white, or gray.

Flexible handpiece 44 is preferably made of a four and one half inch diameter circle of expanded closed cell foam rubber or plastic, preferably reinforced on the finger loop side with a fabric layer. Finger receiving loop 54 is preferably a webbing of elastic material sewn on first and second ends to the flexible handpiece with an adequate spacing therebetween to receive two or three fingers of an average adult, e.g., at approximately two inches, and is centered on the finger loop side. The finger retaining loop 54 may include printed indicia (not shown). FIG. 4 shows the reverse or finger-loop side of the cosmetic abrasive pad of FIG. 3 and FIG. 5 is a cross sectional illustration of the cosmetic abrasive pad of FIG. 3, taken along line 5—5 as shown in FIG. 3 and illustrating the gap 50 between the hook fastener arrays 46, 48.

FIG. 6 illustrates an alternative embodiment of the cosmetic abrasive pad 60 having a larger circular flexible hand piece 62 having a hand loop side opposing an abrasive retaining side and carrying or bearing first and second elongate, straight strips of hook fasteners 64, 66 for attachment to a substantially rectangular abrasive pad segment 70 comprising a segment of lofty, fibrous, non-woven structure of preferably mixed denier organic (e.g., nylon or polyester) preferably crimped or bent filaments bonded at contacting points with a binder such as a thermosetting resin or the like and containing finely divided, biocompatible, soft abrasive. Abrasive segment 70 is detachably attached to the strips of hook fasteners 64, 66 carried on the abrasive retaining side of flexible hand piece 62, as shown in FIG. 6. Abrasive segment 70 has a shorter rectangular dimension of approximately six inches and a longer dimension of approximately nine inches; the four corners are preferably radiused in a quarter circular arc.

In an alternative embodiment, the substantially rectangular abrasive segment has a short dimension of approximately four inches and a longer dimension of approximately six inches; the four corners are preferably radiused in a quarter circular arc. The smaller rectangular abrasive segment may also be readily affixed to the smaller handpiece 44 of FIGS. 3, 4 and 5.

FIG. 7 shows the reverse or hand-loop side of the cosmetic abrasive pad 60, carrying a hand receiving loop 72 made of one inch wide elastic webbing or the like. FIG. 8 is a cross sectional illustration of the cosmetic abrasive pad 60, taken along line 8—8 as shown in FIG. 6. Abrasive segment 70 is detachably attached to elongate strips or arrays of hooks 64, 66 carried on the abrasive retaining side and separated by an elongate gap 68, as best seen in FIGS. 6 and 8. The two hook fasteners arrays 64, 66 include a plurality of hook fasteners (e.g., VELCRO® brand hook fasteners) and releasably engage the fibers of abrasive segment 70 permitting the user to adjust the position of abrasive segment 70 on hand piece 62. The user can manipulate and bend or flex hand piece 62 along the elongate gap 68 so that cosmetic abrasive pad 70 can be readily folded or bent around contours of the body while scrubbing in accordance with the method of the present invention. The user can reverse abrasive segment 70 by switching the side engaged with the hook fastener arrays 64, 66, thereby permitting the use of both sides of abrasive segment 70 before cleaning accumulated detritus out of the abrasive segment.

Flexible handpiece 62 is preferably made of a six inch diameter circle of resilient flexible closed cell foam plastic and is preferably textured on the hand loop side. Hand receiving loop 72 is preferably sewn on first and second ends to the flexible handpiece with an adequate spacing therebetween to receive four fingers of an average adult, e.g., at approximately four inches, and is centered on the hand loop side of handpiece 62. The hand retaining loop 72 may also include printed indicia (not shown).

FIGS. 9, 10 and 11 illustrate a small, substantially circular cosmetic abrasive pad 80 with a permanently stitched-on or attached circular abrasive segment 82. FIG. 10 shows the reverse or finger-loop side of cosmetic abrasive pad 80 and FIG. 11 is a cross sectional illustration of cosmetic abrasive pad 80, taken along line 11—11 as shown in FIG. 9. Cosmetic abrasive pad 80 is advantageously configured for safe, convenient use by a person scrubbing oneself in the home; abrasive segment 82 comprises a substantially circular segment of lofty, fibrous, non-woven structure of preferably mixed denier organic (e.g., nylon or polyester) preferably crimped or bent filaments bonded at contacting points with a binder such as a thermosetting resin or the like and containing finely divided, biocompatible, soft abrasive. Abrasive segment 82 is stitched or attached to a substantially circular and planar flexible hand piece 84 having a finger loop side opposing an abrasive side, as best seen in FIGS. 10 and 11. The user can flex hand piece 84 so that cosmetic abrasive pad 82 can be readily bent around contours of the body while scrubbing, in accordance with the method of the present invention. The abrasive segment 82 can be any of a number of attractive colors, including green, burgundy, white, or gray. Flexible handpiece 84 is preferably made of a four and one half inch diameter circle of expanded closed cell foam rubber or plastic, preferably reinforced on the finger loop side with a fabric layer and carries a finger receiving loop 86 which preferably comprises a webbing of elastic material sewn on first and second ends to the flexible handpiece with an adequate spacing therebetween to receive two or three fingers of an average adult, e.g., at approximately two inches, and centered on the finger loop side, as best seen in FIGS. 10 and 11. The finger retaining loop 86 may include printed indicia (not shown).

FIG. 12 illustrates a cosmetic abrasive pad mitt 100 of the present invention with first and second permanently stitched or attached abrasive segments 110, 112. FIG. 13 is a cross sectional illustration of the cosmetic abrasive pad mitt 100, taken along line 13—13 as shown in FIG. 12, and shows first and second abrasive segments 110, 112, preferably of differing grades of coarseness or abrasive aggressiveness, stitched together, preferably in a continuous outer hem or seam 113 to provide a laminated structure including first and second interior layers of a soft, porous fabric 114, 116 (e.g., a synthetic fabric velour) to form a scrubbing mitt 100 having an opening 118 sized to receive a user's hand (not shown). The two layers of interior fabric 114, 116 are layered together and form an interior lining. The two abrasive segments 110, 112 are positioned on opposing sides of mitt 100, as best seen in FIG. 13, and are preferably disposed to present abrasive exterior surfaces having differing grades of abrasive so that a user can select and use either side by rotating the inserted hand within the mitt 100 to select the appropriate cosmetic abrasive pad surface for scrubbing, to remove detritus or the like from the skin. In the exemplary embodiment of FIG. 13, abrasive pad segment 110 comprises a segment of lofty, fibrous, non-woven structure of preferably mixed denier organic (e.g., nylon or polyester) preferably crimped or bent filaments bonded at contacting points with a binder such as a thermosetting resin or the like and containing finely divided, biocompatible, soft abrasive; whereas opposing abrasive pad segment 112 comprises a more aggressively abrasive segment of lofty, fibrous, non-woven structure of preferably mixed denier organic (e.g., nylon or polyester) preferably crimped or bent filaments bonded at contacting points with a binder such as a thermosetting resin or the like and preferably containing a more coarsely divided, biocompatible, harder abrasive, as compared to the abrasive of first abrasive segment 110.

The cosmetic abrasive pad mitt 100 is preferably finished with seam binding 120 stitched along the outer seam 113; seam binding 120 is preferably made of the same fabric as the interior fabric layers 14, 116. The free edges of opening 118 also preferably include seam binding such that the first abrasive pad segment 110 is preferably stitched with seam binding 122 to first fabric layer 114 and second abrasive pad segment 112 is preferably stitched with seam binding 122 to second fabric layer 116.

Abrasive mitt may be formed from two substantially rectangular abrasive pad segments or abrasive pad segments of any shape which will accommodate all or part of the hand through an opening. In the embodiment of FIGS. 12 and 13, mitt 100 has a semicircularly rounded closed distal end 126 opposite the proximal opening 118.

Figure 14:
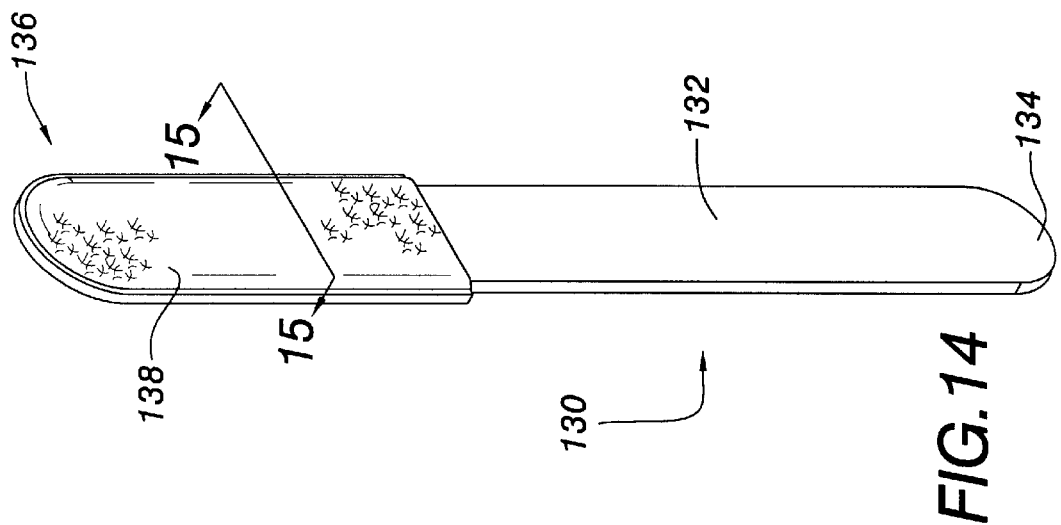
FIG. 14 illustrates a cosmetic abrasive pad including an elongate handle carrying a cosmetic abrasive segment in accordance with the present invention.

Turning now to another embodiment, FIG. 14 illustrates a cosmetic abrasive pad 130 including an elongate handpiece or handle 132 having a proximal end 134 opposite a distal end 136 carrying a cosmetic abrasive segment 138 in accordance with the present invention.

Figure 15:
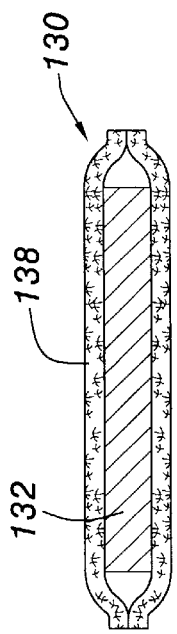
FIG. 15 is a cross sectional illustration of the cosmetic abrasive pad of FIG. 14, taken along line 15—15 as shown in FIG. 14.

FIG. 15 is a cross sectional illustration of cosmetic abrasive pad 130, taken along line 15—15 as shown in FIG. 14 and illustrating that abrasive segment 138 is bonded to and wrapped around the periphery of elongate handle 132 and comprises a segment of lofty, fibrous, non-woven structure of preferably mixed denier organic (e.g., nylon or polyester) preferably crimped or bent filaments bonded at contacting points with a binder such as a thermosetting resin or the like and containing finely divided, biocompatible, soft abrasive.

Elongate handle 132 is preferably a substantially rigid, smooth and planar member preferably made of plastic or wood, having the configuration of a tongue depressor.

Figure 16:
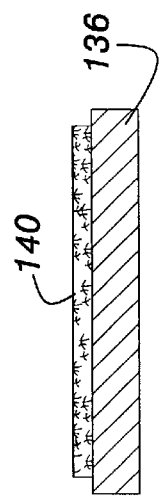
FIG. 16 is a cross sectional illustration of an alternative embodiment of the cosmetic abrasive pad of FIG. 14.

FIG. 16 is a cross sectional illustration of an alternative embodiment of the cosmetic abrasive pad of FIG. 14 but differs in that the distal end of handle 132 carries an abrasive pad segment 140 on only one side of the handle.

Figure 17:
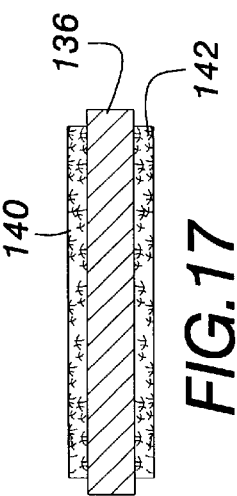
FIG. 17 is a cross sectional illustration of another alternative embodiment of the cosmetic abrasive pad of FIG. 14.

FIG. 17 is a cross sectional illustration of another alternative embodiment of the cosmetic abrasive pad of FIG. 16, and includes a first, fine cosmetic abrasive pad 140 on a side opposing a second side carrying a second cosmetic abrasive pad 142. In the exemplary embodiment of FIG. 17, abrasive pad segment 140 comprises a segment of lofty, fibrous, non-woven structure of preferably mixed denier organic (e.g., nylon or polyester) preferably crimped or bent filaments bonded at contacting points with a binder such as a thermosetting resin or the like and containing finely divided, biocompatible, soft abrasive; whereas opposing abrasive pad segment 142 comprises a more aggressively abrasive segment of lofty, fibrous, non-woven structure of preferably mixed denier organic (e.g., nylon or polyester) preferably crimped or bent filaments bonded at contacting points with a binder such as a thermosetting resin or the like and preferably containing a more coarsely divided, biocompatible, harder abrasive, as compared to the abrasive of first abrasive segment 140.

As noted above, in the cosmetic method of the present invention, a user removes detritus including dead skin cells, oxidized sebum, soil, and other foreign matter from the horny corneal layer of the epidermis by grasping the cosmetic abrasive pad of the present invention (e.g., 80) including the abrasive segment (e.g., 82), and wiping the surface of the epidermis with the cosmetic abrasive pad to remove at least part of the dead skin cells of the horny corneal layer of the epidermis and accumulating the removed dead skin cells in the lofty, fibrous, non-woven structure of the abrasive segment. The method may also include the steps of washing, immersing, bathing or rinsing the epidermis in water and/or soap, lotion, oil, facial creme or other cosmetic preparations, after which, the epidermis and cosmetic abrasive pad may be rinsed in clean water and dried.

The cosmetic abrasive pad segment material (e.g., 30) is specifically described as a uniform, lofty, open, non-woven, three-dimensional, lightweight web formed of many interlaced randomly disposed, flexible, durable, tough organic fibers exhibiting substantial resiliency and strength upon prolonged subjection to water, oils, soaps or cosmetic lotions. Fibers of the web are preferably bent or crimped nylon or polyester and are firmly bonded together at points where they intersect and contact one another by globules of an organic (e.g., resin) binder, thereby forming a three-dimensionally integrated structure. Distributed within the web and firmly adhered by binder globules at variously spaced points along the fibers are the biocompatible abrasive (e.g., pumice) particles. The many interstices between adjacent fibers remain substantially unfilled by the binder and abrasive particles, thereby providing a composite structure of extremely low density having a network of many relatively large intercommunicated interstitial voids 32. The voids 32 preferably make up approximately three-fourths or more of the total volume occupied by the composite structure. The resulting abrasive cosmetic pad structure is flexible and readily compressible and, upon subsequent release of pressure, essentially completely recovers to the initial uncompressed form. The resulting lightweight, lofty, extremely open, fibrous, abrasive construction exhibits a remarkably effective and unique abrasive action and, in use, acculates detritus 36; the pad is essentially non-clogging and non-filling in nature, particularly when used in conjunction with liquids such as water or cosmetic lotions or oils. Since the fibers are resilient and yieldable, the biocompatible abrasive particles are extremely effective at removing dead skin or other detritus from the epidermis at pressures a lay person would use when scrubbing one's self.

As noted above, commercially available uniform, lofty, open, non-woven, three-dimensional, lightweight abrasive web material is available from the Minnesota Mining and Manufacturing (3M) Company and is sold for commercial and industrial applications under the tradename Scotch-Brite™, as described in U. S. Pat. No. 2,958,593 to Hoover et al, U.S. Pat. No. 4,078,340 to Klecker et al and U.S. Pat. No. 5,363,604 to Heyer, the entire disclosures of which are incorporated herein by reference. Specific reference is made to the photograph of FIG. 1 in U.S. Pat. No. 2,958,593, illustrating the globules of binder carrying abrasive particles and showing the open, lofty structure defining the voids between the filaments in the structure which the applicant has discovered is so well suited to gently abrading and exfoliating the epidermis and accumulating the detritus from the horny corneal layer of the over skin.

By using relatively non-aggressive and biocompatible abrasive particles, such as pumice, a cosmetic abrasive pad (e.g., 40) including a uniform, lofty, open, non-woven, three-dimensional, lightweight web formed of many interlaced randomly disposed, flexible, durable, tough organic fibers exhibiting substantial resiliency and strength upon prolonged subjection to water, oils, soaps or cosmetic lotions is produced and is usable in the method of the present invention.

Having described preferred embodiments of a new and improved cosmetic method and cosmetic abrasive pad, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A cosmetic method for removing detritus including dead skin cells from an horny corneal layer of an epidermis, comprising: inserting a user's hand within a mitt including a first cosmetic abrasive pad having a first segment of lofty, fibrous, non-woven structure mixed denier filament; said filaments contacting one another at contacting points and being bonded to one another at said contacting points; said contacting points being bonded with a binder and carrying biocompatible abrasive particles; and wiping the surface of the epidermis with the cosmetic abrasive mitt to remove at least part of the dead skin cells of the horny corneal layer of the epidermis, and accumulating removed skin cells in said lofty, fibrous, non-woven structure mixed denier filaments carrying biocompatible abrasive particles.

2. The method of claim 1 further including the step of:

rotating the hand within the mitt to bring to bear a second cosmetic abrasive pad having a second segment of lofty, fibrous, non-woven structure mixed denier filaments;

said filaments contacting one another at contacting points and being bonded to one another at said contacting points; said contacting points being bonded with a binder and carrying a second grade of biocompatible abrasive particles finer than the particles on the first abrasive pad segment; and wiping the surface of the epidermis with said second cosmetic abrasive pad.

3. A cosmetic method for removing detritus including dead skin cells from an horny corneal layer of an epidermis, comprising: grasping a proximal end of an elongated handle carrying a cosmetic abrasive pad on a handle distal end, said cosmetic abrasive padding including a segment of lofty, fibrous, non-woven structure of mixed denier filaments; said filaments contacting one another at contacting points and being bonded to one another at said contacting points; said contacting points being bonded with a binder and carrying biocompatible abrasive particles; and wiping the surface of the epidermis with the cosmetic abrasive pad to remove at least part of the dead skin cells of the horny corneal layer of the epidermis, and accumulating the removed dead skin cells in said lofty, fibrous, non-woven structure mixed denier filaments carrying biocompatible abrasive particles.

4. The method of claim 3 when said wiping step comprises wiping the surface of the skin between adjacent toes to remove dead skin cells from between the toes.

5. A cosmetic abrasive pad for use in scrubbing a section of skin to remove detritus, comprising:

a handpiece carrying a segment of lofty, fibrous, non-woven structure of crimped or bent filaments; said filaments contacting one another at contacting points and being bonded to one another at said contacting points and defining a plurality of interstitial voids therebetween; said contacting points being bonded with a binder and containing biocompatible abrasive particles; and said handpiece comprising a flexible mitt having an opening sized to receive at least part of a user's hand and having first and second opposing sides, wherein at least one side of said mitt is covered in said segment of lofty, fibrous, non-woven structure of mixed denier filaments; said filaments contacting one another at contacting points and being bonded to one another at said contacting points; said contacting points being bonded with a binder and containing biocompatible abrasive particles.

6. The cosmetic abrasive pad of claim 5, wherein said flexible mitt first side includes said segment of lofty, fibrous, non-woven structure of mixed denier filaments; said filaments contacting one another at contacting points and being bonded to one another at said contacting points; said contacting points being bonded with a binder and containing biocompatible abrasive particles of a first coarseness;

wherein said second side further includes a second segment of lofty, fibrous, non-woven structure of mixed denier filaments; said filaments contacting one another at contacting points and being bonded to one another at said contacting points; said contacting points being bonded with a binder and containing coarser biocompatible abrasive particles as compared to the first coarseness of said biocompatible abrasive particles of said segment carried on said first side, said second segment being carried on said second side.

7. A cosmetic abrasive pad for use in scrubbing a section of skin to remove detritus, comprising:

a handpiece carrying a segment of lofty, fibrous, non-woven structure of crimped or bent filaments; said filaments contacting one another at contacting points and being bonded to one another at said contacting points and defining a plurality of interstitial voids therebetween; said contacting points being bonded with a binder and containing biocompatible abrasive particles; and said handpiece comprising a substantially rigid elongate handle having a proximal end opposing a distal end carrying a segment of lofty, fibrous, non-woven structure of mixed denier filaments; said filaments contacting one another at contacting points and being bonded to one another at said contacting points; said contacting points being bonded with a binder and containing biocompatible abrasive particles.

8. The cosmetic abrasive pad of claim 7, said elongate handle having a first side opposing a second side and said segment of lofty, fibrous, non-woven structure of mixed denier filaments; said filaments contacting one another at contacting points and being bonded to one another at said contacting points; said contacting points being bonded with a binder and containing biocompatible abrasive particles being carried on said first side.

9. The cosmetic abrasive pad of claim 7, further including a second segment of lofty, fibrous, non-woven structure of mixed denier filaments; said filaments contacting one another at contacting points and being bonded to one another at said contacting points; said contacting points being bonded with a binder and containing coarser biocompatible abrasive particles as compared to the biocompatible abrasive particles of said segment carried on said first side, said second segment being carried on said second side.

* * * * *